(12) United States Patent
Sauerwein et al.

(10) Patent No.: US 11,280,747 B2
(45) Date of Patent: Mar. 22, 2022

(54) MEASUREMENT SYSTEM AND METHOD FOR OPERATING A MEASUREMENT SYSTEM

(71) Applicant: RayScan Technologies GmbH, Meersburg (DE)

(72) Inventors: Christoph Sauerwein, Überlingen (DE); Michael Krumm, Überlingen (DE)

(73) Assignee: RAYSCAN TECHNOLOGIES GMBH, Meersburg (DE)

( * ) Notice: Subject to any disclaimer, the term of this patent is extended or adjusted under 35 U.S.C. 154(b) by 0 days.

(21) Appl. No.: 16/348,072

(22) PCT Filed: Nov. 8, 2017

(86) PCT No.: PCT/EP2017/078633
§ 371 (c)(1),
(2) Date: May 7, 2019

(87) PCT Pub. No.: WO2018/087159
PCT Pub. Date: May 17, 2018

(65) Prior Publication Data
US 2019/0353601 A1    Nov. 21, 2019

(30) Foreign Application Priority Data
Nov. 8, 2016    (DE) .......................... 102016013315.5

(51) Int. Cl.
*G01N 23/04*    (2018.01)
*G01N 23/18*    (2018.01)
(Continued)

(52) U.S. Cl.
CPC ............. *G01N 23/04* (2013.01); *A61B 6/032* (2013.01); *A61B 6/035* (2013.01); *A61B 6/44* (2013.01);
(Continued)

(58) Field of Classification Search
CPC ........... A61B 6/032; A61B 6/035; A61B 6/44; A61B 6/4405; A61B 6/4411;
(Continued)

(56) References Cited

U.S. PATENT DOCUMENTS 6,092,928 A * 7/2000 Mattson ................... A61B 6/08
378/197
6,155,713 A * 12/2000 Watanabe ............ A61B 6/4441
378/197
(Continued)

FOREIGN PATENT DOCUMENTS

DE    199 58 864 A1    6/2001
DE    102 15 982 A1    11/2003
(Continued)

OTHER PUBLICATIONS

International Search Report and Written Opinion issued in PCT/EP2017/078633 dated Feb. 9, 2018.
(Continued)

*Primary Examiner* — Allen C. Ho
(74) *Attorney, Agent, or Firm* — Butzel Long

(57) ABSTRACT

A method for operating a measurement system (100) comprises: generating a beam of electromagnetic radiation (25) directed along a central ray (27) using a radiation source (19); moving the radiation source (19) relative to an object region (35) so that the central ray (27) is directed onto a radiation detector (31) during the movement; wherein the moving of the radiation source (19) relative to the object region (35) comprises: rotating the radiation source (19) about a first axis of rotation (D1), wherein the radiation source (19) is disposed eccentrically to the first axis of rotation (D1); rotating the radiation source (19) about a second axis of rotation (D2), wherein the first axis of
(Continued)

rotation (D1) and the second axis of rotation (D2) together enclose an acute angle (α) amounting to at most 80°.

29 Claims, 5 Drawing Sheets

(51) Int. Cl.
G01N 23/046 (2018.01)
A61B 6/00 (2006.01)
G01V 5/00 (2006.01)
A61B 6/03 (2006.01)

(52) U.S. Cl.
CPC .......... *A61B 6/4405* (2013.01); *A61B 6/4411* (2013.01); *A61B 6/4429* (2013.01); *A61B 6/4435* (2013.01); *A61B 6/4441* (2013.01); *A61B 6/4447* (2013.01); *A61B 6/4452* (2013.01); *A61B 6/4458* (2013.01); *A61B 6/4476* (2013.01); *A61B 6/4482* (2013.01); *G01N 23/046* (2013.01); *G01N 23/18* (2013.01); *G01V 5/005* (2013.01); *G01V 5/0016* (2013.01); *G01V 5/0066* (2013.01); *G01N 2223/308* (2013.01); *G01N 2223/33* (2013.01)

(58) Field of Classification Search
CPC ... A61B 6/4429; A61B 6/4435; A61B 6/4441; A61B 6/4447; A61B 6/4452; A61B 6/4458; A61B 6/4476; A61B 6/4482; G01N 23/04; G01N 23/046; G01N 23/18; G01V 5/0016; G01V 5/005; G01V 5/0066
USPC .............. 378/57, 58, 62, 196–198, 205, 189
See application file for complete search history.

(56) References Cited

U.S. PATENT DOCUMENTS

| | | | | |
|---|---|---|---|---|
| 6,200,024 | B1 | 3/2001 | Negrelli | |
| 6,325,537 | B1 * | 12/2001 | Watanabe | A61B 6/4233 378/196 |
| 6,428,206 | B1 * | 8/2002 | Watanabe | A61B 6/4233 378/197 |
| 6,435,715 | B1 | 8/2002 | Betz et al. | |
| 6,459,760 | B1 * | 10/2002 | D'Ambrosio | G01N 23/04 378/43 |
| 6,496,558 | B2 * | 12/2002 | Graumann | A61B 6/0478 378/197 |
| 6,582,121 | B2 * | 6/2003 | Crain | A61B 6/107 378/189 |
| 6,592,259 | B2 * | 7/2003 | Crain | A61B 6/107 378/196 |
| 6,711,235 | B2 * | 3/2004 | Galish | G21K 1/025 378/147 |
| 6,733,176 | B2 * | 5/2004 | Schmitt | A61B 6/4464 378/196 |
| 6,869,217 | B2 | 3/2005 | Rasche et al. | |
| 6,872,000 | B2 * | 3/2005 | Atzinger | A61B 6/4233 378/197 |
| 6,934,352 | B2 * | 8/2005 | Freytag | A61B 6/032 378/4 |
| 6,935,779 | B2 * | 8/2005 | Zhang | A61B 6/08 378/196 |
| 7,003,070 | B1 * | 2/2006 | Chen | A61B 6/00 378/17 |
| 7,018,097 | B2 * | 3/2006 | Schmitt | A61B 6/4441 378/197 |
| 7,073,939 | B2 * | 7/2006 | Spahn | A61B 6/488 378/196 |
| 7,401,977 | B2 * | 7/2008 | Graumann | A61B 6/4441 378/197 |
| 7,441,952 | B2 * | 10/2008 | Häupl | A61B 6/4464 378/189 |
| 7,441,953 | B2 * | 10/2008 | Banks | A61B 5/1038 378/197 |
| 7,500,784 | B2 * | 3/2009 | Grebner | A61B 6/4441 378/193 |
| 7,515,677 | B2 * | 4/2009 | Zellerhoff | A61B 6/4441 378/196 |
| 7,530,739 | B2 * | 5/2009 | Lurz | A61B 6/4441 378/197 |
| 7,641,391 | B2 * | 1/2010 | Schwieker | A61B 6/4464 378/197 |
| 7,748,900 | B2 * | 7/2010 | Maschke | A61B 6/4458 378/198 |
| 7,806,589 | B2 * | 10/2010 | Tashman | A61B 6/505 378/197 |
| 7,837,385 | B2 * | 11/2010 | Klingenbeck-Regn | G03B 42/02 378/197 |
| 7,905,658 | B2 * | 3/2011 | GroEszett | A61B 6/4441 378/193 |
| 7,938,579 | B2 * | 5/2011 | GrosEszett | A61B 6/4458 378/197 |
| 7,942,575 | B2 * | 5/2011 | Fehre | A61B 6/587 378/197 |
| 7,949,094 | B2 * | 5/2011 | Ahn | A61B 6/588 378/57 |
| 7,988,357 | B2 * | 8/2011 | Hornung | A61B 6/4233 378/197 |
| 8,320,517 | B2 * | 11/2012 | Dennerlein | A61B 6/032 378/4 |
| 8,459,867 | B2 * | 6/2013 | Muller | A61B 6/4458 378/196 |
| 8,534,915 | B2 | 9/2013 | Maschke | |
| 8,534,916 | B2 * | 9/2013 | Maschke | A61B 6/486 378/197 |
| 8,606,348 | B2 * | 12/2013 | Maschke | A61B 90/37 600/427 |
| 8,767,920 | B2 * | 7/2014 | Spahn | A61B 6/4464 378/117 |
| 8,944,680 | B2 * | 2/2015 | Graumann | A61B 6/4476 378/197 |
| 8,989,846 | B2 * | 3/2015 | Kuduvalli | A61N 5/1048 600/427 |
| 9,107,633 | B2 * | 8/2015 | Muller | A61B 6/4441 |
| 9,200,948 | B2 * | 12/2015 | Jan | A61B 6/035 |
| 9,225,770 | B2 * | 3/2016 | Omura | A61B 6/4458 |
| 10,015,872 | B2 * | 7/2018 | Diehm | A61B 6/4007 |
| 10,136,866 | B2 * | 11/2018 | Onobori | A61B 6/4283 |
| 10,561,384 | B2 * | 2/2020 | Tanaka | A61B 6/4452 |
| 10,667,772 | B2 * | 6/2020 | Mikami | A61B 90/50 |
| 10,674,977 | B2 * | 6/2020 | Nabeta | A61B 6/4458 |
| 10,765,388 | B2 * | 9/2020 | Nozawa | A61B 6/00 |
| 10,772,587 | B2 * | 9/2020 | Sanbuichi | A61B 6/40 |
| 10,856,821 | B2 * | 12/2020 | Onobori | A61B 6/4283 |
| 10,905,389 | B2 * | 2/2021 | Ogura | A61B 6/4405 |
| 10,945,689 | B2 * | 3/2021 | Eguchi | A61B 6/4405 |
| 10,952,689 | B2 * | 3/2021 | Cox | A61B 6/4464 |
| 10,993,682 | B2 * | 5/2021 | Nabeta | A61B 6/4405 |

FOREIGN PATENT DOCUMENTS

| | | |
|---|---|---|
| DE | 10 2004 057 004 A1 | 6/2006 |
| DE | 10 2006 028 327 B3 | 1/2008 |
| DE | 699 38 384 T2 | 4/2009 |
| DE | 10 2010 020 603 A1 | 11/2011 |
| JP | 2012-189560 A | 10/2012 |

OTHER PUBLICATIONS

German Office Action dated Jun. 23, 2017 for corresponding DE Application No. 10 2016 013 315.5.

* cited by examiner

MEASUREMENT SYSTEM AND METHOD FOR OPERATING A MEASUREMENT SYSTEM

The invention relates to a measurement system and a method for operating a measurement system. The method and the measurement system can be used to analyze objects and connections between objects using electromagnetic radiation (for example X-radiation, gamma radiation). In particular, the method and the measurement system serve for analyzing of material connections (for example weld seams, solder joints, adhesive joints, etc.) in complex formed objects such as a car body and the same.

Conventional measurement systems using X-radiation (X-ray system) comprise a radiation source and a radiation detector wherein the radiation source and the radiation detector are fixedly disposed, i. e. immobile relative to each other, at a support. Therein, the radiation source and the radiation detector are disposed opposite to each other so that an object to be analyzed can be disposed between the radiation source and the radiation detector.

Due to the support, at which the radiation source and the radiation detector are fixedly disposed, it is difficult to analyze complex formed objects and in particular welding seams of a complex formed object using the conventional X-radiation systems. Due to the fact that the object to be analyzed must be disposed between the radiation source and the radiation detector, that the radiation source and the radiation detector are fixedly connected to the support, and that the object must be moved relative to the radiation source and the radiation detector for tomography, only a limited region of the object to be analyzed can be disposed between the radiation source and the radiation detector and be analyzed while avoiding collision of the support and the object.

In particular, this problem arises during use of conventional X-radiation systems when the spatial structure of the object is to be analyzed using X-ray tomography. For analyzing of the spatial structure, the object to be analyzed is illuminated from mutually different spatial directions using X-radiation generated by the radiation source, whereby multiple recordings of the same volume region of the object can be recorded from different directions. For this, it is necessary to move the object to be analyzed and the assembly of the radiation source and the radiation detector relative to each other. However, as described above, the freedom for arranging complex formed objects in conventional X-radiation systems is limited.

Therefore, it is an objective of the present invention to provide a measurement system and a method for operating a measurement system which allow for an analysis of complex formed objects, in particular their spatial structure.

According to an aspect of the present invention, a method for operating a measurement system comprises: generating a beam of electromagnetic radiation using a radiation source, wherein the beam is directed along a central ray of the beam; moving the radiation source relative to an object region so that the central ray is directed onto a radiation detector and the object region, respectively, during the movement; wherein the moving of the radiation source comprises: rotating the radiation source about a first axis of rotation, wherein the radiation source is disposed eccentrically to the first axis of rotation; and rotating the radiation source about a second axis of rotation, wherein the first axis of rotation and the second axis of rotation together enclosed an acute angle amounting to at most 80°, in particular at most 70° or at most 60°.

Here, the central ray is to be understood as a ray of the beam of electromagnetic radiation which is located in the center of the beam. For example, the emission characteristic of the radiation source has a maximum in a direction of the central ray.

For example, the radiation source is an electrically operated radiation source. It generates the beam from the energy supplied to it. For example, the energy can be provided in form of a high-voltage which is provided via a high-voltage source, for example. The high-voltage source and the radiation source can be connected electrically to each other via an energy supply cable (for example a high-voltage cable). Alternatively, the energy can be provided via a battery which, in particular, is mounted to the radiation source.

Further alternatively, the radiation source can be a radioactive source which generates electromagnetic radiation by radioactive decay.

The object region is a spatial region in which an object to be analyzed can be disposed. According to the method, the object region is illuminated using the beam of electromagnetic radiation from different directions because the radiation source is moved relative to the object region. During the movement of the radiation source, the radiation source is oriented so that the central ray is directed onto a radiation detector of the measurement system, in particular onto a center of a detection area of the radiation detector.

The moving of the radiation source comprises the rotating of the radiation source about a first axis of rotation. For example, the first axis of rotation can intersect the object region. During the rotation of the radiation source about the first axis of rotation, the radiation source is the disposed eccentrically to the first axis of rotation, i. e. the radiation source, in particular the location of the radiation source where the radiation is emitted, is disposed at a distance different from zero from the first axis of rotation. During the rotation, this distance can be maintained constant or can be varied. By varying the distance between the radiation source and the first axis of rotation, the direction from which the central ray is incident onto the object region can be changed. Accordingly, by varying the distance, the radiation source can be adjusted optimally relative to the object region.

The moving of the radiation source relative to the object region further comprises the rotating of the radiation source about a second axis of rotation. The second axis of rotation is different from the first axis of rotation. In particular, the rotation of the radiation source about the second axis of rotation can be performed during the rotation of the radiation source about the first axis of rotation, i. e. simultaneously. The second axis of rotation can intersect the object region. In particular, the first and the second axis of rotation can intersect in the object region.

The distance of the radiation source to the second axis of rotation can be small compared to the distance of the radiation source to the first axis of rotation. In particular, the second axis of rotation intersects the radiation source so that, during the rotation of the radiation source about the first axis of rotation, the radiation source is always disposed at the second axis of rotation (and rotates about it). In particular, the second axis of rotation can be disposed essentially parallel to the central ray.

The first axis of rotation and the second axis of rotation together enclose an acute angle. Herein, an angle between two axes is understood as the angle at the point of intersection of both of the axes. When the axes are skewed to each other, i. e. the axes do not have a common point of intersection, then the angle between both of the axes is to be understood as the angle formed between the first axis and the projection of the second axis along the shortest connection of both of the axes onto the first axis.

Two axes are essentially parallel to each other when the angle formed between them is smaller than 10°, in particular smaller than 5° or smaller than 1°.

In other words, the movement of the radiation source can be described as follows: The first axis of rotation and the second axis of rotation together enclose an acute angle amounting to at most 80°, in particular at most 70° or at most 60°. The second axis of rotation is rotated about the first axis of rotation, and the radiation source is rotated about the second axis of rotation. Therein, the radiation source is disposed eccentrically to the first axis of rotation.

The method can be performed using an apparatus adapted, by configuration, so that the acute angle between the first axis of rotation and the second axis of rotation is not adjustable to more than 80°, in particular is not adjustable to more than 70° or is not adjustable to more than 60°. For example, the apparatus can be the measurement system described hereinafter. For example, the freedom of movement of the elements providing the first axis of rotation and the second axis of rotation is limited, by configuration of a controller controlling the elements or by the configuration of mechanics constituting the elements, so that the acute angle between the first axis of rotation and the second of axis of rotation is not adjustable to more than a 80°, in particular not adjustable to more than 70° or not adjustable to more than 60°.

For this, the apparatus can comprise elements providing the first axis of rotation and the second axis of rotation. By a controller of the apparatus, the apparatus and the elements of the apparatus, respectively, can be controlled so that the acute angle between the first axis of rotation and the second axis of rotation is not adjustable to more than 80°, in particular not adjustable to more than 70° or not adjustable to more than 60°. In other words, the elements of the apparatus are controlled so that the acute angle between the first axis of rotation and the second axis of rotation is not adjustable to more than 80°, in particular not adjustable to more than 70° or not adjustable to more than 60°.

According to another embodiment of the method, the acute angle between the first axis of rotation and the second axis of rotation amounts to at least 10°, in particular at least 20° or at least 30°.

The method according to this embodiment can be performed using an apparatus adapted, by configuration, so that the acute angle between the first axis of rotation and the second axis of rotation is not adjustable to less than 10°, in particular not adjustable to less than 20° or not adjustable to less than 30°. For example, the apparatus can be the measurement system described hereinafter. For example, the freedom of movement of the elements providing the first and the second axis of rotation is limited, by the configuration of a controller controlling the elements or by the configuration of mechanics constituting the elements, so that the acute angle between the first axis of rotation and the second axis of rotation is not adjustable to less than 10°, in particular not adjustable to less than 20° or not adjustable to less than 30°.

For this, the apparatus can comprise elements providing the first axis of rotation and the second axis of rotation. By a controller of the apparatus, the apparatus and the elements of the apparatus, respectively, can be controlled so that the acute angle between the first axis of rotation and the second axis of rotation is not adjustable to less than 10°, in particular not adjustable to less than 20° or not adjustable to less than 30°. In other words, the elements of the apparatus are controlled so that the acute angle between the first axis of rotation and the second axis of rotation is not adjustable to less than 10°, in particular not adjustable to less than 20° or not adjustable to less than 30°.

According to another embodiment of the method, the rotation of the radiation source about the first axis of rotation and the rotation of the radiation source about the second axis of rotation are performed in opposite directions of rotation.

The direction of rotation of the rotation of the radiation source about an axis of rotation can be right-handed or left-handed. The directions of rotation are the same when the radiation source is rotated right-handed about the first axis of rotation as well as about the second axis of rotation or when the radiation source is rotated left-handed about the first axis of rotation as well as about the second axis of rotation. The directions of rotation are opposite when the radiation source is rotated right-handed about the first axis of rotation and left-handed about the second axis of rotation or when the radiation source is rotated left-handed about the first axis of rotation and right-handed about the second axis of rotation.

In order to define the directions of rotation of two axes not being parallel to each other, the following definition applies: The rotation of the radiation source about the first and the second axis of rotation are performed in the same directions of rotation when the projection of the rotation about the first axis of rotation onto an axis and the protection of the rotation about the second axis of rotation onto said axes, which is not perpendicular to each of the first axis of rotation and the second axis of rotation, have the same direction of rotation. For example, the axis can be the first or the second axis of rotation. Accordingly, the rotation of the radiation source about the first axis of rotation and the rotation of the radiation source about the second axis of rotation are performed in opposite directions of rotation when the rotations projected onto said axes are performed in opposite directions.

According to another embodiment, the angular velocity of the rotation of the radiation source about the first axis of rotation is equal to the angular velocity of the rotation of the radiation source about second axis of rotation.

According to another embodiment, the method further comprises: rotating the radiation detector about a third axis of rotation, wherein the radiation detector is disposed eccentrically to the third axis of rotation.

In this embodiment, not only the radiation source is rotated about the first and the second axis of rotation, but also the radiation detector is rotated about a third axis of rotation. The rotation of the radiation detector about the third axis of rotation is performed during the rotation of the radiation source about the first axis of rotation, i. e. simultaneously to the rotation of the radiation source about the first axis of rotation. Therein, the radiation detector is disposed eccentrically to the third axis of rotation, i. e. disposed at a distance different from zero to the third axis of rotation. During the rotations of the radiation source and the radiation detector, both are oriented relative to each other so that the central ray is directed onto the radiation detector, in particular onto a center of a detection area of the radiation detector.

The distance between the third axis of rotation and a center of a detection area of the radiation detector can be adjusted in dependence of the desired magnification of the object section to be analyzed. The magnification is essentially determined by the angle between the first axis of rotation and the central ray of the beam as well as the distance of the object section to the radiation detector. The distance between the third axis of rotation and a center of a detection area of the radiation detector can, depending on the particular application, amount to at least 1 cm and/or at most 16 m, for example.

In particular, the first axis of rotation and the third axis of rotation can be oriented essentially parallel to each other. In particular, the first and third axis of rotation can line up.

A ratio of the distance of the radiation source from the first axis of rotation to the distance of the center of a detection area of the radiation detector from the third axis of rotation can amount to at least 1/20, in particular at least 1/10 or at least 1/5 and/or at most 20/1, and particular at most 10/1 or at most 5/1, for example.

The rotation of the radiation source about the first axis of rotation and the rotation of the radiation detector about the third axis of rotation can be performed in the same directions of rotation and/or phase-shifted about essentially 180° to each other and/or with the same angular velocity.

To each other phase-shifted about essentially 180° means that the phase-shift differs from 180° by ε of at most 10°. When the first and the third axis of rotation line up, the phase-shift of 180° means that the first and the third axis of rotation is located between the radiation source and the radiation detector. During rotation with the same angular velocity, the phase-shift, i. e. the relative rotation position of the radiation source to the radiation detector, is maintained. When the radiation source and the radiation detector in addition rotate in the same directions of rotation about the first and third axis of rotation, respectively, the phase-shift is maintained constant.

The method described above can be used for operating a measurement system in which the radiation source is supported by a first robot and the radiation detector is supported by a second robot different from the first robot. The measurement system can be adapted so that the first robot can freely move the radiation source, i. e. translate and rotate it relative to the (spatially fixed) reference system of the object region, and so that the second robot can freely move the radiation detector.

According to another aspect of the present invention, a measurement system comprises a radiation detector configured to detect electromagnetic radiation; a radiation source oriented towards the radiation detector, wherein the radiation source is configured to generate a beam of electromagnetic radiation and to emit the beam of electromagnetic radiation along a central ray of the beam; a first movement apparatus configured to move the radiation source relative to an object region; wherein the first movement apparatus comprises a first base element and a first cantilever beam bearing-mounted to the first base element, wherein the first cantilever beam is rotatable relative to the first base element about a first axis of rotation; wherein the radiation source is rotatable to relative to the first cantilever beam about a second axis of rotation; wherein the first axis of rotation and the second axis of rotation together enclose an acute angle amounting to at most 80°, in particular at most 70° or at most 60°.

"Bearing-mounted" means that the first cantilever beam and the first base element are connected to each other while the first cantilever beam is movable relative to the first base element, i. e. translatable and/or rotatable. In particular, this means that the first cantilever beam is directly connected, i. e. without another element providing a bearing, to the first base element.

The above-described measurement system provides those degrees of freedom necessary for performing the above-described method. The above-described measurement system allows to illuminate an object disposed in the object region from different directions using the beam of electromagnetic radiation and to detect of the radiation penetrating the object using the radiation detector.

The measurement system can be adapted, by configuration, so that the acute angle between the first axis of rotation and the second axis of rotation is not adjustable to more than 80°, in particular not adjustable to more than 70° or not adjustable to more than 60°. For example, a controller of the first movement apparatus or mechanics constituting the first movement apparatus is/are configured so that the acute angle between the first axis of rotation and the second axis of rotation is not adjustable to more than 80°, in particular not adjustable to more than 70° or not adjustable to more than 60°.

The acute angle between the first axis of rotation and the second axis of rotation can amount to at least 10°, in particular at least 20° or at least 30°, for example. This ensures that the object region is illuminated from different directions.

For this, the measurement system can be adapted, by configuration, so that the acute angle between the first axis of rotation and the second axis of rotation is not adjustable to less than 10°, in particular not adjustable to less than 20° or not adjustable to less than 30°. For example, a controller of the first movement apparatus or mechanics constituting the first movement apparatus is/are configured so that the acute angle between the first axis of rotation and the second axis of rotation is not adjustable to less than 10°, in particular not adjustable to less than 20° or not adjustable to less than 30°.

The radiation source can be disposed eccentrically to the first axis of rotation, i. e. the radiation source is disposed at a distance different from zero to the first axis of rotation.

The second axis of rotation and the central ray can be oriented essentially parallel to each other. The first and the second axis of rotation can intersect the object region and, in particular, intersect each other in the object region. In this configuration, the central ray runs approximately on the surface of a cone, the apex of which is disposed in the object region, while the radiation source performs a circular motion, seen in a plane perpendicular to the first axis of rotation, for example.

According to another embodiment, the measurement system further comprises a first actuator configured to rotate the first cantilever beam about the first axis of rotation. In this embodiment, the actuator effects the rotation of the first cantilever beam about the first axis of rotation.

According to an embodiment therein, the radiation source is bearing-mounted to freely rotate about the second axis of rotation. In this embodiment, the orientation of the radiation source relative to the first cantilever beam does not result from an actuator, but only from the bearing-mounting of the radiation source to the cantilever beam and the force of gravity. While the first actuator rotates the first cantilever beam about the first axis of rotation, the radiation source freely rotates about the second axis of rotation.

According to an alternative embodiment, a second actuator can be provided configured to rotate the radiation source about the second axis of rotation, and a controller can be provided configured to control the first and the second actuator. In particular, the controller can be configured to control the first and second actuator so that the first cantilever beam and the radiation source are rotated about the first and the second axis of rotation, respectively, in opposite directions of rotation and/or with the same angular velocity.

According to another embodiment, the measurement system comprises a second movement apparatus configured to move the radiation detector relative to the object region, wherein the second movement apparatus comprises a second base element and a second cantilever beam bearing-mounted to the second base element, wherein the second cantilever beam is rotatable relative to the second base element about a third axis of rotation, and wherein the radiation detector is disposed at the second cantilever beam.

In this embodiment, further to the radiation source, also the radiation detector is bearing-mounted for rotation. The radiation detector can be fixedly mounted to the second cantilever beam, i. e. be fixedly connected to it. Further, the radiation detector can be disposed eccentrically to the third axis of rotation, i. e. at a distance from the third axis of rotation. A distance between the third axis of rotation and the center of a detection area of the radiation detector can amount to at least 1 cm and/or at most 16 m, for example.

The first axis of rotation and the third axis of rotation can be oriented essentially parallel to each other and, in particular, line up. A ratio of the length of the first cantilever beam to the length of the second cantilever beam can be at least 1/20, in particular at least 1/10 or at least 1/5, and/or at most 20/1, in particular at most 10/1 or at most 5/1, for example. The length of the cantilever beam is to be understood as its extent along a direction of the cantilever beam along which the extent is largest.

A detection area of the radiation detector and the third axis of rotation together enclose an angle which can amount to between 10° and 90°. Accordingly, the detection area of the radiation detector can be tilted so that the central ray is incident perpendicularly onto the detection area or is incident onto the detection area at an oblique angle.

The measurement system can further comprises a third actuator configured to rotate the second cantilever beam about the third axis of rotation, wherein the controller is further configured to control the third actuator so that the first and the second cantilever beam are rotated about the first and the third axis of rotation, respectively, in the same directions of rotation and/or phase-shifted about essentially 180° to each other and/or with the same angular velocity.

The measurement system can further comprise a first robot and a second robot different from the first robot, wherein the first robot supports the first base element and wherein the second robot supports the second base element. The first and the second base element can be fixedly connected to further components of the first and the second robot, respectively, or be bearing-mounted thereon. The first and the second robot are configured to position and orientate the first base element and the second base element relative to each other. It may be provided that, during operation of the measurement system, firstly the first and the second base element are positioned and orientated relative to each other by controlling the first and second robot accordingly. After the first and the second base element are positioned relative to each other, both are neither displaced nor rotated relative to each other during the remainder of the method. However, it can be provided that the entire assembly of the first and the second base element is displaced and/or rotated relative to the object region by controlling the first and the second robot.

According to another embodiment, the measurement system further comprises a frame, wherein the first base element and the second base element are fixedly connected to the frame. In contrast to the previous description of the measurement system, according to which the first and the second base element are supported by two different robots and therefore are freely movable relative to each other within the limits of the degrees of freedom of the individual robots, this embodiment provides that the first and the second base element are fixedly connected to each other via a frame. I. e. the first base element cannot be moved relative to the frame and the second base element cannot be moved relative to the frame because both of them are each fixedly connected to the frame or are a part of the frame.

This embodiment provides the advantage that the radiation source (and the radiation detector) is each freely movable relative to the frame, but the assembly of the radiation source and the radiation detector can be displaced and rotated easily as a whole due to the common frame. In particular, this means that the first and the third axis of rotation have a fixed spatial arrangement to each other which, due to the frame, can be moved as a whole without change.

In contrast to the embodiment, in which two different robots are used for disposing the radiation source and the radiation detector, the stable positioning of the radiation source and the radiation detector relative to each other is significantly simplified in this embodiment due to the rigid frame. Therein, the frame can be adapted so that it limits the freedom of movement of the assembly of the radiation source and the radiation detector only slightly.

The frame can be supported by a single robot so that the assembly of the radiation source and the radiation detector can be moved simply without thereby changing the relative position and orientation of the radiation source to the radiation detector.

Although the first and the second base element are fixedly disposed relative to each other due to the frame, the radiation source and the radiation detector can be moved independently from each other relative to each other by the first (and the second) cantilever beam. Therefore, the measurement system can be free of a structure fixedly connecting the radiation source and the radiation detector to each other. I. e., the measurement system does not comprise an element fixedly connecting the radiation source and the radiation detector to each other.

A distance between the radiation source and the radiation detector can amount to at least 5 cm and/or at most 20 m.

The length direction of the first cantilever beam and the first axis of rotation together enclose an acute angle which can amount to between 30° and 90°. In particular, the first cantilever beam and the element of the measurement system providing the first axis of rotation can, by configuration, be configured so that the acute angle between the length direction of the first cantilever beam and the first axis of rotation is not adjustable to less than 30° and is not adjustable to more than 90°. Thereby, a simple and comfortable bearing between the radiation source and the first cantilever beam can be used while avoiding collision of the spatially extended radiation source to the first cantilever beam during the rotation of the first cantilever beam about the first axis of rotation.

Further, the first cantilever beam can have a movement element at which the radiation source is disposed and which is displaceable along the first cantilever beam. Therein, the radiation source is bearing-mounted to the movement element to rotate about the second axis of rotation. Due to the movement element which is displaceable along the first cantilever beam, for example by an actuator, the distance of the radiation source to the first axis of rotation as well as the direction along which the central ray is directed onto the object region can be adjusted. Therein, the ability to rotate the radiation source about the second axis of rotation is provided by a bearing at the movement element.

In the above-described embodiments, the central ray and a detection area of the radiation detector can together enclose an acute angle of less than 80°, less than 70° or less than 60°, and/or more than 50°, in particular more than 55° or more than 60°. Further, the second axis of rotation and a detection area of the radiation detector can together enclose an acute angle of less than 80°, in particular less than 70° or less than 60°, and/or more than 50°, in particular more than 55° or more than 60°. The first axis of rotation and the central ray can together enclose an acute angle amounting to at least 10°, in particular at least 20° or at least 30°, and/or at most 80°, in particular at most 70° or at most 60°.

The first, second and third axis of rotation can be mutually different, and the first and the second cantilever beam can be different from each other.

The radiation generated by the radiation source can be electromagnetic radiation, photon radiation, gamma radiation or X-radiation, for example. The radiation can have an energy in the range of 10 keV to 30 MeV.

Hereinafter, different embodiments of a measurement system and a method of operating a measurement system are described with reference to the accompanying drawings.

First, a method for operating a measurement system is described with reference to FIGS. 1 to 3.

Figure 1:
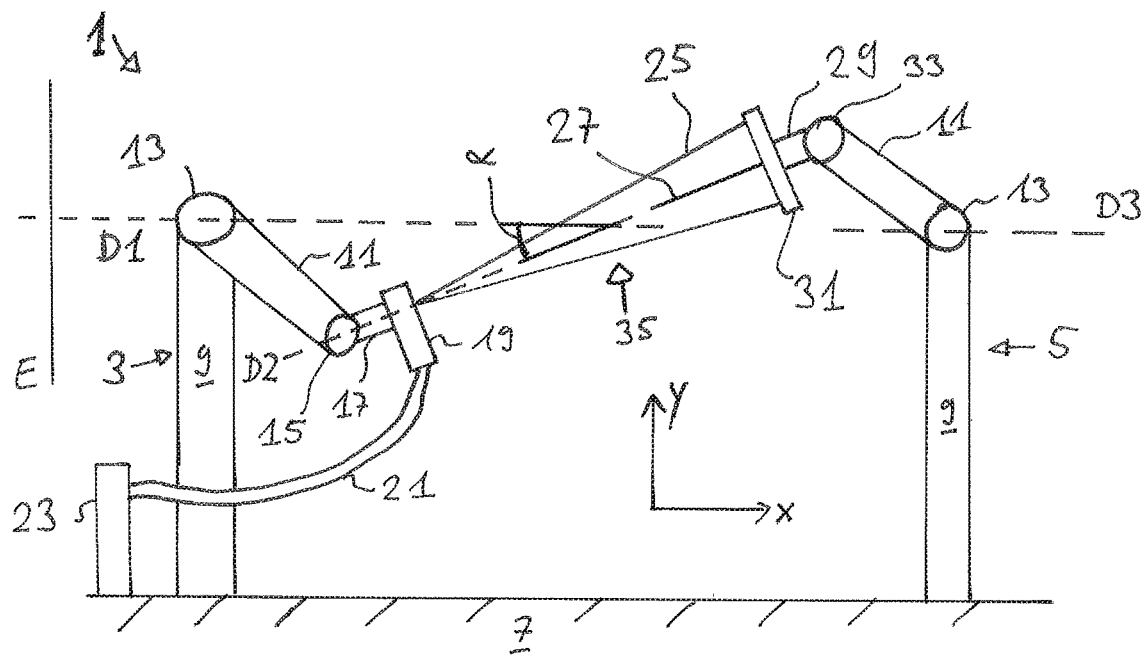
FIG. 1 shows a measurement system for illustration of a method of operating a measurement system.
Figure 2:
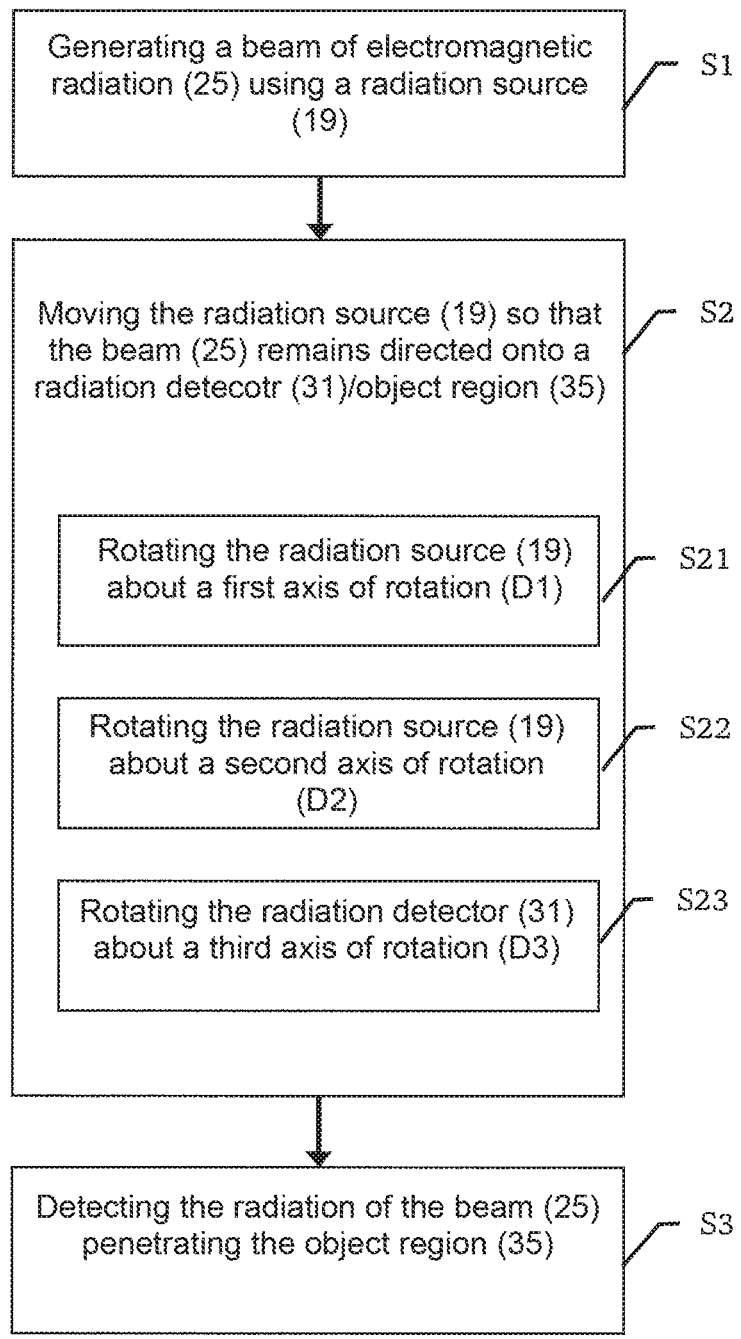
FIG. 2 shows an embodiment of a method for operating a measurement system.

FIG. 1 shows a measurement system 1 comprising a first robot 3 and a second robot 5, each mounted on the floor 7. Each of the first robot 3 and the second robot 5 has a base unit 9 and an arm 11, for example, connected to each other via a joint 13. Via the joint 13, the arm 11 is bearing-mounted to the base unit 9, i.e. movable relative to the base unit 9 about at least one degree of freedom.

The joint 13 of the first robot 3 is adapted so that the arm 11 of the first robot 3 is bearing-mounted to the base unit 9 to be rotatable relative to the base unit 9 of the first robot 3 about at least a first axis of rotation D1 (dashed line). In FIG. 1, the first axis of rotation D1 extends within the plane of drawing.

The first robot 3 comprises another joint 15 bearing-mounting a holder 17 at the arm 11 of the first robot 3. The joint 15 is configured so that the holder 17 can be rotated relative to the arm 11 about a second axis of rotation D2 (dashed line) relative to the arm 11.

The holder 17 connects a radiation source 19 to the first robot 3. By the degrees of freedom provided by the first robot 3, the radiation source 19 can be rotated about the first axis of rotation D1 and the second axis of rotation D2.

In this example, the radiation source 19 is an X-ray tube, for example, electrically connected to a high-voltage source 23 via a high-voltage cable 21. The high-voltage source 23 supplies a high-voltage to the radiation source 19 and the radiation source 19 uses the high-voltage to generate a beam of electromagnetic radiation 25 (for example X-radiation). A central ray 27 is in the center of the beam 25.

In another example, the radiation source 19 is an open chamber (for example an aperture having the shape of a cone) in which radioactive isotopes can be disposed. A delivery hose 21 connects the chamber to a radioactive isotopes working container 23. The radioactive isotopes are provided in the radioactive isotopes working container 23 and are subsequently conveyed to the chamber via the delivery hose 21. When radioactive isotopes are disposed in the chamber, the radioactive isotopes generate, by decay, a beam of electromagnetic radiation 25, in the center of which a central ray 27 is located.

The radiation source 19 is disposed eccentrically to the first axis of rotation D1, i. e. the radiation source 19 has a distance different from zero to the axis of rotation D1. Further, the radiation source 19 is disposed so that the first axis of rotation D1 and the second axis of rotation D2 enclose an acute angle α.

The second robot 5 further comprises a holder 29 supporting a radiation detector 31. The holder 29 is connected to the arm 11 of the second robot 5 via a joint 33 bearing-mounting the holder 29 to the arm 11 of the second robot 5.

The joint 13 of the second robot 5 bearing-mounts the arm 11 of the second robot 5 to the base unit 9 of the second robot 5. In particular, the joint 13 is configured so that the arm 11 of the second robot 5 can be rotated relative to the base unit 9 of the second robot 5 about a third axis of rotation D3 (dashed line). The third axis of rotation D3 is disposed in the plane of drawing of FIG. 1.

Hereinbefore, the first robot 3 and the second robot 5 were described, each providing a limited amount of degrees of freedom for positioning the radiation source 19 and the detector 31. However, the first robot 3 and the second robot 5 are not limited to these degrees of freedom/configurations and can, in particular, be configured so that the radiation source 19 and the radiation detector 31 can be moved freely, i.e. be translated and/or rotated.

Hereinafter, a method for operating a measurement system, in particular the measurement system 1 shown in FIG. 1, is described with reference to FIG. 2. The method allows for analysis of an 15 object disposed in an object region 35 (see FIG. 1). The object region 35 is located between the radiation source 19 and the radiation detector 31. The object region 35 is located at a point of intersection of the first axis of rotation D1 and the second axis of rotation D2, for example, or in a region where both axes of rotation are separated by a smallest distance.

The method comprises generating a beam of electromagnetic radiation using a radiation source (step S1). In this example, a beam 25 of X-rays is generated using a radiation source 19 wherein the beam 25 of X-rays is directed along a central ray 27 (see FIG. 1). Instead of X-radiation, other electromagnetic radiation can be used as well.

Further, the method comprises moving the radiation source 19 relative to an object region 35 wherein the movement is performed so that the central ray 27 is directed onto the radiation detector 31 during the movement (step S2). This means that the radiation source 19 and eventually the radiation detector 31 are moved during the movement of the radiation source 19 so that the central ray 27 remains directed onto the radiation detector 31 for the duration of the movement. During the movement of the radiation source 19, the radiation detector 31 detects the radiation of the beam 25 penetrating the object region 35 and being incident onto the radiation detector 31 (step S3).

Therein, the movement of the radiation source 19 comprises rotating the radiation source 19 about a first axis of rotation D1 wherein the radiation source 19 is disposed eccentrically to the first axis of rotation D1 (step S21). During the rotation of the radiation source 19 about the first axis of rotation D1, the distance of the radiation source 19 to the first axis of rotation D1 does not need to be constant and, in particular, can be varied. Further, it can be provided that the radiation source 19 intersects the first axis of rotation D1, i.e. that the distance between them reduces to zero. However, during the majority of the duration of the rotation of the radiation source 19 about the first axis of rotation D1, the radiation source 19 must be disposed eccentrically to the first axis of rotation D1.

The movement of the radiation source 19 further comprises the rotating of the radiation source 19 about a second axis of rotation D2 which together with the first axis of rotation D1 encloses an acute angle α (step S22). The acute angle α can amount to at most 80°, however, also smaller values are possible. Accordingly, the rotation of the radiation source 19 about the first axis of rotation D1 and the second axis of rotation D2 is performed so that the acute angle α amounts to at most 80° during the movement. According to a preferred embodiment, the angle α is also not less than 10° during the movement.

In other words, the movement of the radiation source 19 relative to the object region 35 can be described as follows: The radiation source 19 is rotated about a second axis of rotation D2 which together with the first axis of rotation D1 encloses an acute angle α. The second axis of rotation D2 is rotated about the first axis of rotation D1.

In particular, the first axis of rotation D1 and/or the second axis of rotation D2 can intersect the object region 35 and, in particular, intersect each other therein. The movement of the radiation source 19 is exemplified in FIG. 3.

Figure 3:
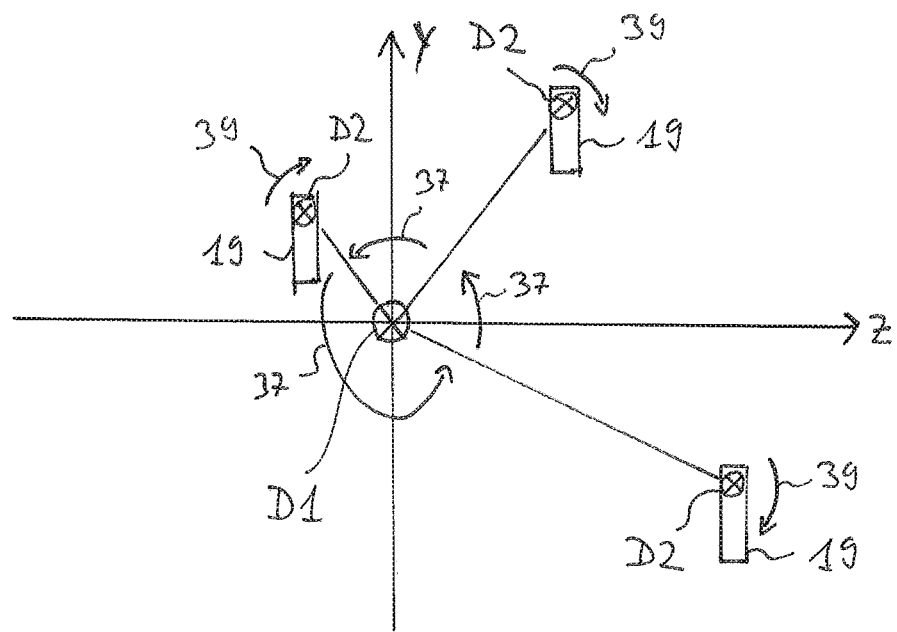
FIG. 3 is a diagram for describing the spatial arrangement of a radiation source of the measurement system during its rotation about a first and a second axis.

FIG. 3 shows an illustration of the rotation of the radiation source 19 about the first axis of rotation D1 and the second axis of rotation D2 for several different points of time during the movement. Specifically, FIG. 3 shows the projection of the rotations onto the plane E shown in FIG. 1 and being oriented perpendicular to the first axis of rotation D1. This corresponds to the view of an observer along the X-axis (see FIG. 1) from the point of intersection of the first axis of rotation D1 with the plane E. This is clarified by the coordinate systems shown in FIGS. 1 and 3.

The arrows indicated by numeral 37 denote the direction of rotation, i.e. the direction of rotation of the radiation source 19 about the first axis of rotation D1. In FIG. 1, this direction of rotation is left-handed, i.e. a counter-clockwise rotation.

The arrows indicated by numeral 39 denote the direction of rotation, i.e. the direction of rotation of the rotation of the radiation source 19 about the second axis of rotation D2. In the example shown in FIG. 3, the direction of rotation of the rotation of the radiation source 19 about the second axis of rotation D2 is right-handed, i.e. a clockwise rotation.

Because the plane of drawing of FIG. 3 is perpendicular to the first axis of rotation D1 but not perpendicular to the second axis of rotation D2 (due to the acute angle α formed between both axes, see FIG. 1), the rotation shown in FIG. 3 about the second axis of rotation D2 is to be understood as the rotation projected onto the plane of drawing of FIG. 3.

As shown in FIG. 3, the direction of rotation of the rotation of the radiation source 19 about the first axis of rotation D1 is opposite to the direction of rotation of the rotation of the radiation source 19 about the second axis of rotation D2. By this, when the angular velocities of the rotations of the radiation source 19 about the first axis of rotation D1 and the second axis of rotation D2, respectively, are equal, which is the case in a preferred embodiment, the rotations cancel each other so that the radiation source 19 is translated, i. e. is displaced in position relative to the object region 35, but not or only slightly rotated in the plane shown in FIG. 3 of the reference system of the object region 35. In the X-Y-coordinate system shown in FIG. 1, the radiation source 19 exhibits tilting about the angle 2α when the distance of the radiation source 19 to the first axis of rotation D1 is maintained constant during the rotation, however the radiation source 19 does not rotate relative to the Y-Z-coordinate system shown in FIG. 3. This provides the advantage that the high-voltage cable 21 which conventionally is thick, heavy and rigid, can easily follow the movement of the radiation source 19.

In addition, the object region 35 is illuminated from different directions during the rotation of the radiation source 19 about the first axis of rotation D1 and the second axis of rotation D2, which is necessary for tomography. During the movement of the radiation source 19, the central ray 27 runs along the surface of a cone, the apex of which is disposed in the object region 35 and the baseline of which corresponds to the position of the radiation source 19, more precisely to the location of emittance of the radiation at the radiation source 19 during the movement, for example.

As shown in FIG. 3, the distance of the radiation source 19 to the first axis of rotation D1 can be varied during the rotation of the radiation source 19 about the first axis of rotation D1. For example, this provides the advantage that a complex formed object to be analyzed is illuminated from directions which are especially advantageous for the tomography.

According to another embodiment, the method can further comprise that the radiation detector 31 is rotated about a third axis of rotation D3, wherein the radiation detector 31 is disposed eccentrically to the third axis of rotation D3, i. e. at a distance different from zero thereto. This step is denoted in FIG. 2 with numeral S23. As also described with reference to the eccentricity of the radiation source 19, also the radiation detector 31 can temporarily intersect the third axis of rotation D3.

In this embodiment, the rotations are adjusted so that the central ray 27 continuously remains directed onto the radiation detector 31, in particular a center of a detection area of the radiation detector 31, during the rotation of the radiation source 19 about the first axis of rotation D1. As shown in FIG. 1, the first axis of rotation D1 and the third axis of rotation D3 can be oriented parallel to each other and, in particular, as shown in FIG. 1, line up.

In contrast to the radiation source 19 which, in addition to the rotation about the first axis of rotation D1 is also rotated about the second axis of rotation D2, it can be provided that the radiation detector 31 is rotated only about the third axis of rotation D3 and not about further axes of rotation during the rotation of the radiation source 19 about the first axis of rotation D1. In this case, the joint 33 of the second robot 5 would be fixedly adjusted and would suppress a rotation of the holder 29 relative to the arm 11 of the second robot 5.

While the rotation of the radiation source 19 about the first axis of rotation D1 is left-handed and the rotation of the radiation source 19 about the second axis of rotation D2 is right-handed as shown in FIG. 3, i. e. in opposite directions of rotation, it can be provided that the rotation of the radiation source 19 about the first axis of rotation D1 and the rotation of the radiation detector 31 about the third axis of rotation D3 are performed in the same directions of rotation and/or phase-shifted about essentially 180° relative to each other and/or with the same angular velocity. In accordance with FIG. 3, the radiation detector 31 would undergo a left-handed, i. e. counter-clockwise, rotation about the third axis of rotation D3. The angle of essentially 180° is measured in the Y-Z-coordinate system of FIG. 3.

Hereinafter, embodiments of a measurement system are described with reference to FIGS. 4 to 7.

Figure 4:
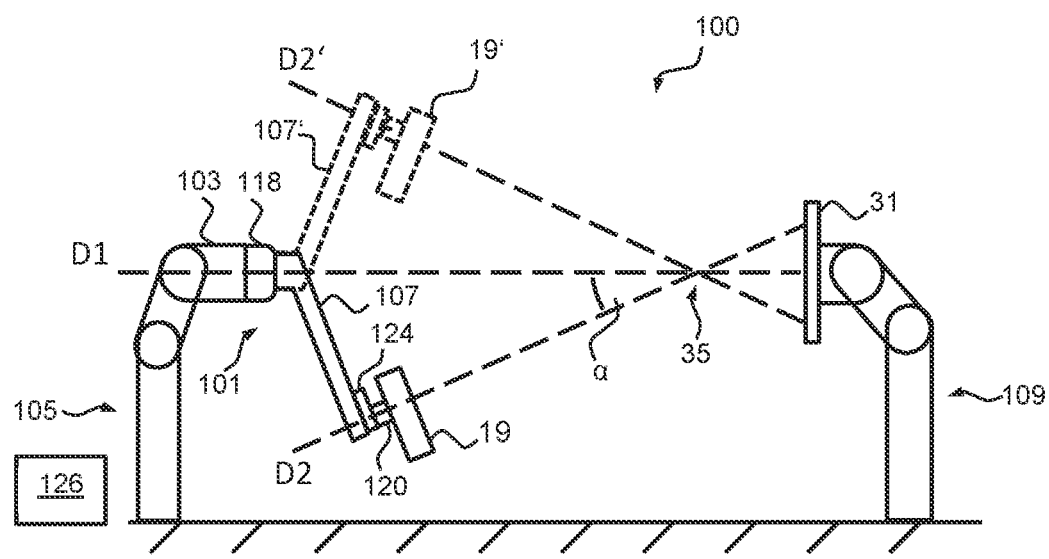
FIG. 4 shows a first embodiment of a measurement system according to the present invention.

FIG. 4 shows a first embodiment of a measurement system 100 according to the present invention. The measurement system 100 comprises a radiation source 19 configured to generate a beam of electromagnetic radiation (for example X-radiation) and to emit the beam along a central ray of 10 the beam (see step S1 in FIG. 2). The beam and the central ray are not shown in FIGS. 4 to 7. They are described with reference to FIG. 1. The measurement system 100 further comprises a radiation detector 31 configured to detect the electromagnetic radiation (see step S3 in FIG. 2).

The measurement system 100 further comprises a first movement apparatus 101 configured to move the radiation source 19 relative to the object region 35. The first movement apparatus 101 comprises a first base element 103 which is a part of a stand or a robot 105. The first movement apparatus 101 further comprises a first cantilever beam 107 bearing-mounted to the first base element 103 to be rotatable about a first axis of rotation D1. Therefore, the first cantilever beam 107 is rotatable relative to the first base element 103 about the first axis of rotation D1. The radiation source 19 is rotatable relative to the first cantilever beam 107 about a second axis of rotation D2. For this, the radiation source 19 can be bearing-mounted directly to the first cantilever beam 107. Alternatively, the first cantilever beam 107 can have a movement element 124 at which the radiation source 19 is bearing-mounted to rotate about the second axis of rotation D2 and which is displaceable along the first cantilever beam 107. Due to the movement element, the position of the radiation source 19 relative to the first cantilever beam 107 can be adjusted and changed. The first movement apparatus 101 provides the movement of the radiation source 19 relative to the object region 35 (see steps S2, S21, S22 in FIG. 2).

The first axis of rotation D1 and the second axis of rotation D2 together enclose an acute angle α amounting to at most 80°.

The radiation detector 31 is supported by a stand or a robot 109. In the present embodiment, the radiation detector 31 is fixedly disposed relative to the object region 35. In particular, the first axis of rotation D1 intersects the radiation detector 31, in particular a center of a detection area of the radiation detector 31. The components of the measurement system 100, in particular the distance between the radiation source 19 and the radiation detector 31 as well as the angle α and the position of the radiation detector 31 relative to the first axis of rotation D1 are adjusted so that, during rotation of the radiation source 19 about the first axis of rotation D1 and the second axis of rotation D2, the central ray is directed and remains directed onto the radiation detector 31.

In dashed illustration, FIG. 4 shows the radiation source 19' and the first cantilever beam 107' in another position during the rotation of the radiation source 19 about the first axis of rotation D1. The first cantilever beam 107' is rotated relative to the cantilever beam 107 about 180° relative to the first base element 103 about the first axis of rotation D1. Thereby, also the second axis of rotation D2 is rotated about the first axis of rotation D1 and, therefore, is denoted by D2'. Accordingly, the radiation source 19 is moved as shown in FIG. 3, wherein in contrast to the illustration of FIG. 3, the distance between the radiation source 19 and the first axis of rotation D1 remains constant.

In accordance with the movement shown in FIG. 3, the direction of rotation of the rotation of the radiation source 19 about the first axis of rotation D1 is opposite to the direction of rotation of the rotation of the radiation source 19 about the second axis of rotation D2. For rotating the first cantilever beam 107 relative to the first base element 103 about the first axis of rotation D1, the measurement system can comprise a first actuator not shown and configured to rotate the first cantilever beam 107 about the first axis of rotation D1. For rotating the radiation source 19 about the second axis of rotation, the radiation source 19 can be bearing-mounted to rotate freely about the second axis of rotation, for example. In this case, the radiation source 19 rotates about the second axis of rotation D2 in accordance with the force of gravity acting onto it. When a radiation source supplied via an energy supply cable (for example a high-voltage cable such as high-voltage cable 21) is used as the radiation source, the free rotation about the second axis of rotation can be determined considerably by the energy supply cable and its pulling force onto the radiation source, respectively. Alternatively, a second actor not shown can be provided configured to rotate the radiation source 19 about the second axis of rotation D2. A controller can control the first and the second actuator so that the first cantilever beam 107 and the radiation source 19 are rotated in opposite directions of rotation and/or with the same angular velocity about the first and the second axis of rotation, respectively (see FIG. 3).

Figure 5:
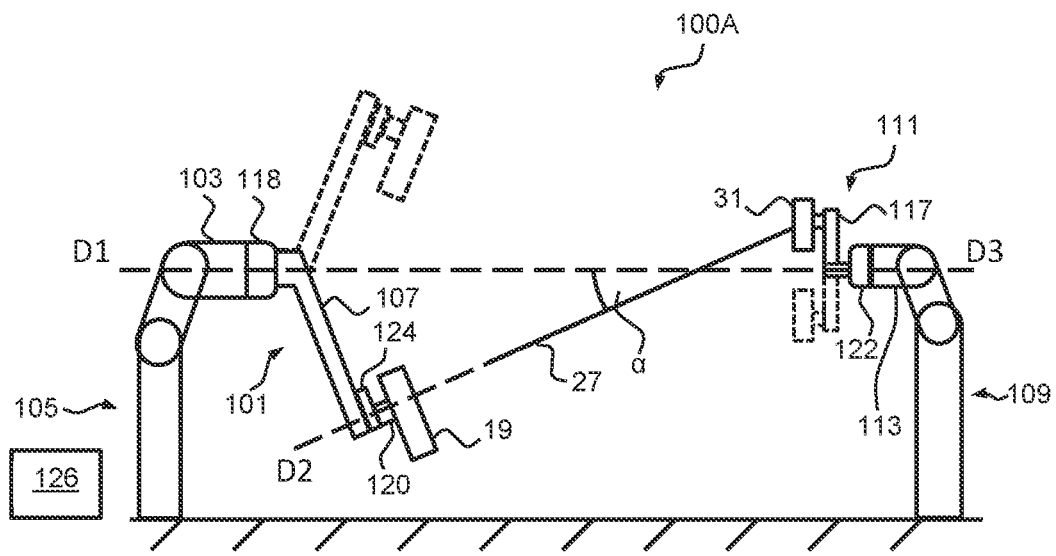
FIG. 5 shows a second embodiment of a measurement system according to the present invention.

FIG. 5 shows a second embodiment of a measurement system according to the present invention. The measurement system 100A comprises the first movement apparatus 101 supported by a stand/robot 105 and being described with reference to FIG. 4.

In contrast to the embodiment shown in FIG. 4, the measurement system 100A (FIG. 5) further comprises a second movement apparatus 111. The second movement apparatus 111 comprises a second base element 113 and a second cantilever beam 117 bearing-mounted to the second base element 113 to rotate about a third axis of rotation D3. Accordingly, the second cantilever beam 117 is rotatable relative to the second base element 113 about the third axis of rotation D3. The radiation detector 31 is disposed at the second cantilever beam 117. In the present example, the radiation detector 31 is disposed eccentrically to the third axis of rotation D3 and fixedly connected to the second cantilever beam 117. Alternatively, the radiation detector can be rotatably connected to the second cantilever beam 117 and/or mounted displaceably on the second cantilever beam 117. Due to this configuration, the radiation detector 31 can be formed smaller as compared to the embodiment shown in FIG. 4. The second movement apparatus 111 provides the movement of the radiation detector about the third axis of rotation (see step S23 in FIG. 2).

A detection area of the radiation detector, onto which the central ray is directed, together with the third axis of rotation D3 can enclose an angle amounting to between 45° and 90°, for example. In FIG. 5, this angle amounts to 90° because of which the central ray 27 is incident onto the detection area of the radiation detector 31 at an oblique angle. Alternatively, the radiation detector 31 can be bearing-mounted in the second base element 113 so that the angle between the detection area of the radiation detector 31 and the third axis of rotation D3 is adjusted so that the central ray 27 is perpendicularly incident onto the radiation detector 31.

As shown in FIG. 5, the first axis of rotation D1 and the third axis of rotation D3 can be orientated parallel to each other and, in particular, as shown in FIG. 5, line up.

Figure 8:
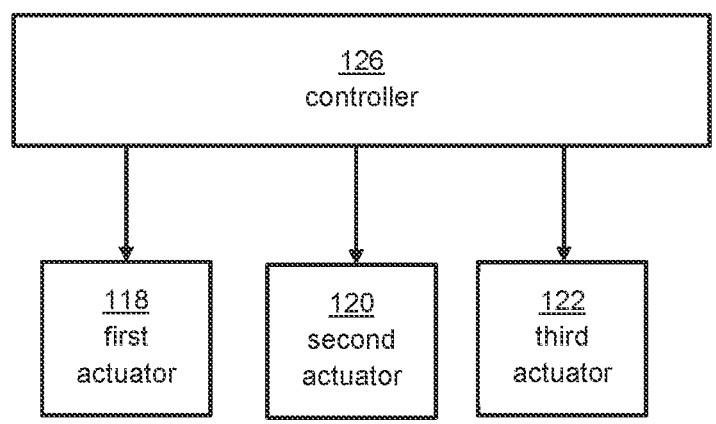
FIG. 8 shows a controller configured to control actuators of a measurement system according to the present invention.

For rotating the second cantilever beam 117 about the third axis of rotation, the measurement system can further comprise a third actuator 122 and configured to rotate the second cantilever beam 117 about the third axis of rotation D3 (relative to the second base element 113). A controller 126 (see FIG. 8) can control the third actuator so that the first cantilever beam 107 and the second cantilever beam 117 are rotated in the same directions of rotation and/or phase-shifted about essentially 180° relative to each other and/or with the same angular velocity about the first axis of rotation D1 and the third axis of rotation D3, respectively.

The first base element 103 can be supported by a first robot 105 and the second base element 113 can be supported by a second robot 109. While the embodiment shown in FIG. 5 has the advantage that the first movement apparatus 101 and the second movement apparatus 111 can be disposed independently from each other by the first robot 105 and the second robot 109, a difficulty exists in that, during the movement of the radiation source 19 about the first and the second axis of rotation, the first axis of rotation D1 and the third axis of rotation D3 are to be disposed in a stable spatial relation to each other. This difficulty is solved by embodiments shown in FIGS. 6 and 7.

Figure 6:
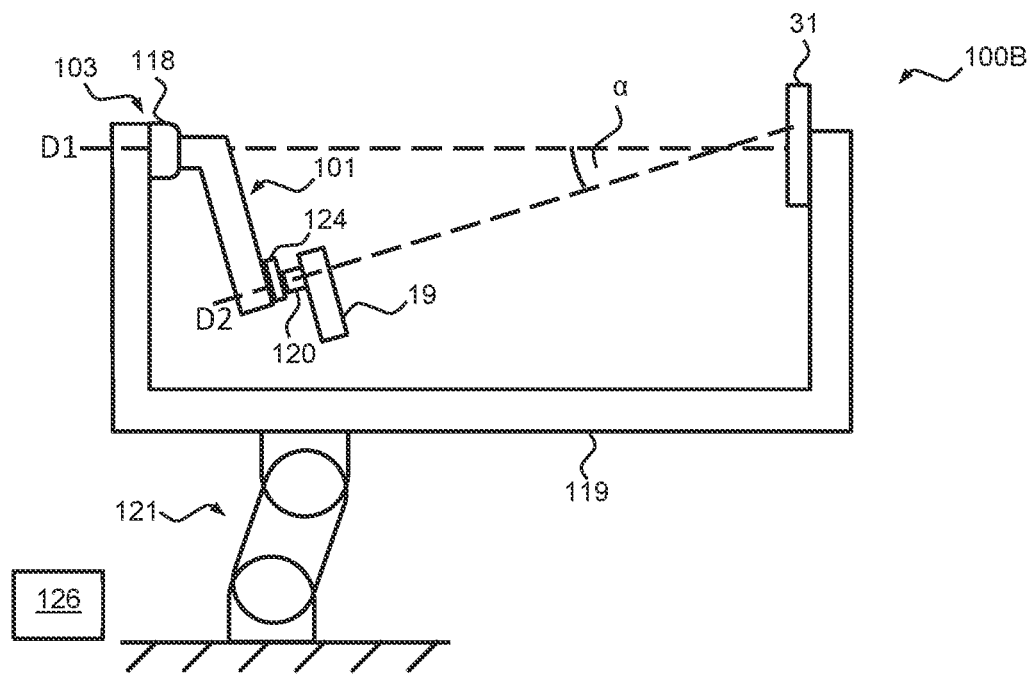
FIG. 6 shows a third embodiment of a measurement system according to the present invention.
Figure 7:
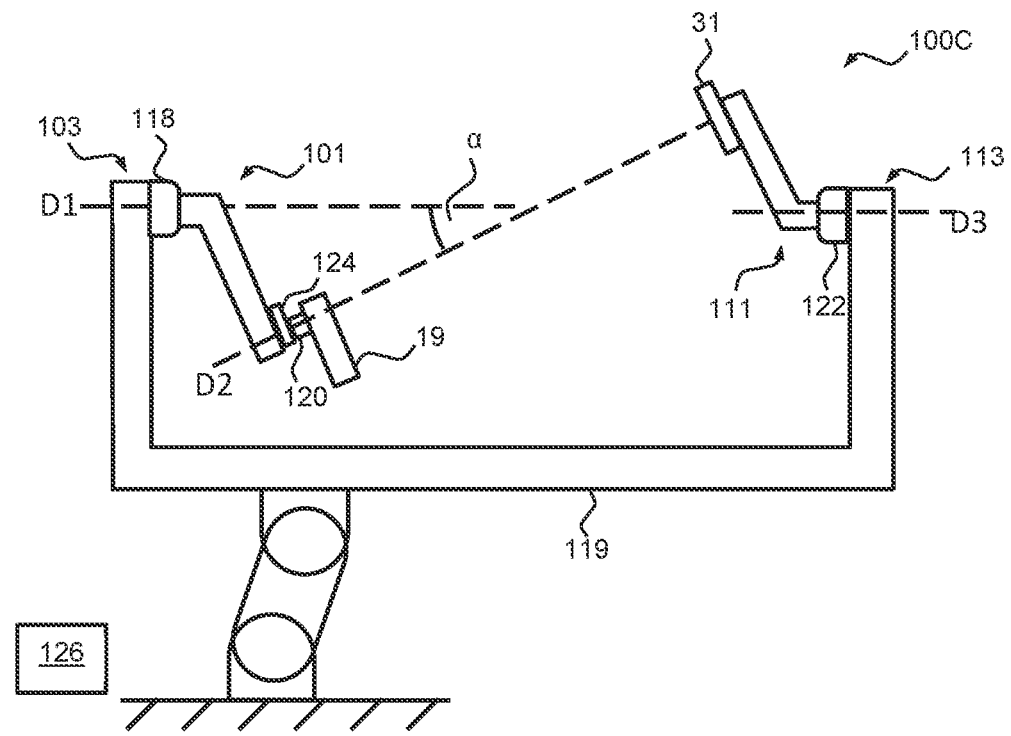
FIG. 7 shows a fourth embodiment of a measurement system according to the present invention.

FIG. 6 shows a third embodiment of a measurement system 100B according to the present invention. FIG. 7 shows a fourth embodiment of a measurement system 100C according to the present invention. The measurement system 100B essentially corresponds to the measurement system 100 shown in FIG. 4, and the measurement system 100C essentially corresponds to the measurement system 100A shown in FIG. 5.

In contrast to the embodiments shown in FIGS. 4 and 5, the first movement apparatus 101 and the second movement apparatus 111 are not supported by different separate stands or robots but by a frame 119 fixedly connecting the first base element 103 of the first movement apparatus 101 to the radiation detector 31 (FIG. 6) and the second base element 113 of the second movement apparatus 111 (FIG. 7), respectively. Therefore, the first base element 103 and the radiation detector 31 of the measurement system 100B are fixedly connected to the frame due to the frame 119. In the measurement system 100C, the first base element 103 and the second base element 113 are fixedly connected to the frame. In particular, the first base element 103 and the second base element 113 can be integral constituting elements of the frame 119 or be fixedly mounted to it. Fixedly means that no connection using a bearing exists between components.

In the example shown in FIG. 7, the detection area of the radiation detector 31 and the third axis of rotation D3 together enclose an angle different from 90°.

As shown in FIGS. 6 and 7, the frame 119 is supported by a robot 121. The robot 121 can dispose the frame 119 and, therefore, the assembly consisting of the radiation source 19 and the radiation detector 31 in space without displacing the first and the third axis of rotation relative to each other. After the frame 119 is positioned, an object to be analyzed can be analyzed simply by rotating the radiation source 19 about the first axis of rotation D1 and the second axis of rotation D2 (and by rotating the radiation detector 31 about the third axis of protection D3) without the necessity to further position the components supporting the base element 103 and the detector 31/the second base element 113, because those are fixedly connected to each other by the frame 119.

The embodiments shown in FIGS. 4 to 7 are further characterized in that the measurement systems are free of a structure fixedly connecting the radiation source 19 and the radiation detector 31 to each other. This means that there is not any element in the measurement system which fixedly connects the radiation source 19 and the radiation detector 31 to each other.

In the above described embodiments, the radiation source 19 and the radiation detector 31 are movable relative to each other and relative to the object region 35 independently from each other due to the first movement apparatus (and the second movement apparatus). This means that the radiation source 19 and the radiation detector 31 are movable relative to each other. This means further that the radiation source 19 can be moved relative to the object region 35 by the first movement apparatus 101 without thereby automatically moving the radiation detector 31 along with it and vice versa.

The invention claimed is:

1. A method for operating a measurement system, the method comprising:
   generating a beam of electromagnetic radiation directed along a central ray using a radiation source;
   moving the radiation source relative to an object region so that the central ray is directed onto a radiation detector during the moving;
   wherein the moving the radiation source relative to the object region comprises:
      rotating the radiation source about a first axis of rotation, wherein the radiation source is disposed eccentrically to the first axis of rotation;
      rotating the radiation source about a second axis of rotation, wherein the first axis of rotation and the second axis of rotation together enclose an acute angle amounting to at most 80°; and
   maintaining the acute angle between the first axis of rotation and the second axis of rotation at not more than 80°.

2. The method according to claim 1,
   wherein the first axis of rotation and the second axis of rotation intersect the object region.

3. The method according to claim 1, wherein at least one of the following is fulfilled:
   the rotating the radiation source about the first axis of rotation and the rotating the radiation source about the second axis of rotation are performed in opposite directions of rotation, and
   an angular velocity of the rotating the radiation source about the first axis of rotation is equal to an angular velocity of the rotating the radiation source about the second axis of rotation, and the acute angle between the first axis of rotation and the second axis of rotation amounts to at least 10°.

4. The method according to claim 1,
   wherein the first axis of rotation and the second axis of rotation are provided by elements of an apparatus; and
   wherein the method further comprises:
      controlling the elements of the apparatus so that the acute angle between the first axis of rotation and the second axis of rotation is not adjustable to less than 10°.

5. The method according to claim 1, further comprising:
   varying a distance between the radiation source and the first axis of rotation during the rotating the radiation source about the first axis of rotation.

6. The method according to claim 1, further comprising:
rotating the radiation detector about a third axis of rotation, wherein the radiation detector is disposed eccentrically to the third axis of rotation.

7. The method according to claim 6, wherein a distance between the third axis of rotation and a center of a detection area of the radiation detector is:
at least 1 cm,
at most 16 m, or
both at least 1 cm and at most 16 m.

8. The method according to claim 6, wherein the first axis of rotation and the third axis of rotation are oriented essentially parallel to each other.

9. The method according to claim 6, wherein a ratio of a distance between the radiation source and the first axis of rotation to a distance between a center of a detection area of the radiation detector and the third axis of rotation is at least 1/20, at most 20/1, or both.

10. The method according to claim 6, wherein the rotating the radiation source about the first axis of rotation and the rotating the radiation detector about the third axis of rotation are performed in at least one of:
a same direction of rotation, and
phase-shifted about 180°+ε, where −10°≤ε≤10°, to each other, and
with a same angular velocity.

11. A measurement system comprising:
a radiation detector configured to detect electromagnetic radiation;
a radiation source oriented towards the radiation detector, wherein the radiation source is configured to generate a beam of electromagnetic radiation and to emit the beam of electromagnetic radiation along a central ray of the beam of electromagnetic radiation;
a first movement apparatus configured to move the radiation source relative to an object region;
wherein the first movement apparatus comprises a first base element and a first cantilever beam bearing-mounted to the first base element, wherein the first cantilever beam is rotatable relative to the first base element about a first axis of rotation;
wherein the radiation source is rotatable relative to the first cantilever beam about a second axis of rotation;
wherein the first axis of rotation and the second axis of rotation enclose an acute angle amounting to at most 80°; and
wherein the acute angle between the first axis of rotation and the second axis of rotation is not adjustable to more than 80°.

12. The measurement system according to claim 11, wherein the acute angle between the first axis of rotation and the second axis of rotation amounts to at least 10°.

13. The measurement system according to claim 12, wherein the acute angle between the first axis of rotation and the second axis of rotation is not adjustable to less than 10°.

14. The measurement system according to claim 11, wherein at least one of the following is fulfilled:
the radiation source is disposed eccentrically to the first axis of rotation, and
the second axis of rotation and the central ray are oriented essentially parallel to each other.

15. The measurement system according to claim 11, further comprising:
a first actuator configured to rotate the first cantilever beam about the first axis of rotation.

16. The measurement system according to claim 15, further comprising:
a second actuator configured to rotate the radiation source about the second axis of rotation;
a controller configured to control the first actuator and the second actuator so that the first cantilever beam and the radiation source are rotated about the first axis of rotation and the second axis of rotation, respectively, in at least one of:
a same direction of rotation, and
with a same angular velocity.

17. The measurement system according to claim 15, wherein the radiation source is bearing-mounted to freely rotate about the second axis of rotation.

18. The measurement system according to claim 11, further comprising:
a second movement apparatus configured to move the radiation detector relative to the object region;
wherein the second movement apparatus comprises a second base element and a second cantilever beam bearing-mounted to the second base element;
wherein the second cantilever beam is rotatable relative to the second base element about a third axis of rotation;
wherein the radiation detector is disposed at the second cantilever beam.

19. The measurement system according to claim 18, wherein at least one of the following is fulfilled:
the radiation detector is fixedly mounted to the second cantilever beam, and
the radiation detector is disposed eccentrically to the third axis of rotation, and
a distance between the third axis of rotation and the center of a detection area of the radiation detector is at least 1 cm, at most 16 m, or both.

20. The measurement system according to claim 18, wherein at least one of the following is fulfilled:
the first axis of rotation and the third axis of rotation are oriented essentially parallel to each other, and
a ratio of a length of the first cantilever beam to a length of the second cantilever beam is at least 1/20, at most 20/1, or both.

21. The measurement system according to claim 18, wherein a smallest angle between the detection area of the radiation detector and the third axis of rotation is between 10° and 90°.

22. The measurement system according to claim 18, further comprising:
a first actuator configured to rotate the first cantilever beam about the third axis of rotation; and
a third actuator configured to rotate the second cantilever beam about the third axis of rotation; and
a controller configured to control the third actuator so that the first cantilever beam and the second cantilever beam are rotated about the first axis of rotation and the third axis of rotation, respectively, in at least one of:
the same directions of rotation,
phase-shifted about 180°+ε, where −10°≤ε≤10°, to each other, and
with a same angular velocity.

23. The measurement system according to claim 18, further comprising:
a first robot supporting the first base element; and
a second robot supporting the second base element, the second robot being different from the first robot.

24. The measurement system according to claim 18, further comprising:
a frame, wherein the first base element and the second base element are fixedly connected to the frame.

25. The measurement system according to claim 24, further comprising:
a robot supporting the frame.

26. The measurement system according to claim 11, wherein the measurement system is free of a structure fixedly connecting the radiation source and the radiation detector to each other.

27. The measurement system according to claim 11, wherein a length direction of the first cantilever beam and the first axis of rotation enclose an acute angle amounting to between 30° and 90°.

28. The measurement system according to claim 11, wherein a distance between the radiation source and the radiation detector is at least one of: at least 5 cm, and at most 20 m.

29. The measurement system according to claim 11, wherein the first cantilever beam has a movement element at which the radiation source is disposed and which is displaceable along the first cantilever beam, and
  wherein the radiation source is bearing-mounted to the movement element to rotate about the second axis of rotation.

\* \* \* \* \*